United States Patent
Murakami

[19]

[11] Patent Number: 6,132,979
[45] Date of Patent: *Oct. 17, 2000

[54] CYTOTOXICITY TESTING METHOD

[75] Inventor: Toru Murakami, Tokyo, Japan

[73] Assignee: NEC Corporation, Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 09/085,647

[22] Filed: May 27, 1998

[30] Foreign Application Priority Data

May 27, 1997 [JP] Japan ................................ 9-136886

[51] Int. Cl.⁷ ................................................ G01N 33/567
[52] U.S. Cl. ............................................................ 435/7.21
[58] Field of Search ........................... 435/240.243, 174, 435/176, 177, 178, 179, 180, 181, 182, 240.22, 240.23, 240.1, 226, 29, 721, 395, 305.1, 32, 11, 25; 424/574; 436/34

[56] References Cited

U.S. PATENT DOCUMENTS

| | | | |
|---|---|---|---|
| 5,066,580 | 11/1991 | Lee | 435/7.21 |
| 5,175,092 | 12/1992 | Gabriels, Jr. | 435/29 |
| 5,221,622 | 6/1993 | Chen | 435/226 |
| 5,314,805 | 5/1994 | Haugland et al. | 435/29 |
| 5,470,739 | 11/1995 | Akaike et al. | 435/402 |
| 5,534,416 | 7/1996 | Millard et al. | 436/34 |
| 5,573,942 | 11/1996 | Miyamoto | 435/402 |
| 5,591,627 | 1/1997 | Miyamoto | 435/289.1 |
| 5,597,703 | 1/1997 | Murakami | 435/25 |
| 5,602,029 | 2/1997 | Miyamoto | 435/395 |
| 5,654,135 | 8/1997 | Tinois et al. | 24/93.1 |
| 5,702,915 | 12/1997 | Miyamoto | 435/32 |
| 5,736,352 | 4/1998 | Murakami | 435/11 |
| 5,792,945 | 8/1998 | Murakami | 73/64.48 |

FOREIGN PATENT DOCUMENTS

| | | |
|---|---|---|
| 63-295963 | 12/1988 | Japan . |
| 63295963 | 12/1988 | Japan . |
| 5-336996 | 12/1993 | Japan . |
| 7-123999 | 5/1995 | Japan . |

OTHER PUBLICATIONS

Millard et al, 1995, Abstracts of the General Meeting of the American Society of Microbiology, vol. 95(0), p. 477, #Q440.

"Cytotoxicity Testing Methods", *The Institute of Tissue Culture Engineers of Japan*, 1991, Asakura Publishing Company, pp. 66–101, In Japanese.

*Primary Examiner*—James C. Housel
*Assistant Examiner*—Ginny Allen Portner
*Attorney, Agent, or Firm*—Sughrue, Mion, Zinn, Macpeak & Seas, PLLC

[57] ABSTRACT

A cytotoxicity testing method of the present invention allows live cells to be directly and accurately counted one by one in order to determine the survival rate of cells. This allows the toxicity of a chemical substance to be quantized with high accuracy.

8 Claims, 2 Drawing Sheets

CYTOTOXICITY TESTING METHOD

BACKGROUND OF THE INVENTION

The present invention relates to a cytotoxicity testing method and, more particularly, to a method of quantizing the toxicity of a chemical substance by counting live cells and dead cells.

The object of toxicity tests for chemical substances is to estimate the danger of the substances to human beings. For such tests, use has customarily been made of higher animals including Mammalia and lower Vertebrata including fishes. Today, however, toxicity tests using animals are being replaced with cytotoxicity tests using the cultured cells of higher animals.

Conventional cytotoxicity testing methods will hereinafter be described with reference to "Cytotoxicity Testing Methods", the Institute of Tissue Culture Engineers of Japan, 1991, Asakura Publishing Company. A first testing method uses the obstruction of the growth of cells as an index. Cells reached a logarithmic growth stage are implanted in a plastic laboratory dish and then cultured for 24 hours in a 37° C. carbon dioxide incubator. After the cells have fully adhered to the dish and again started to grow, a chemical substance to be tested and diluted by a culture fluid such that the final content will coincide with a preselected content is directly added to the culture fluid. On the elapse of 24 hours, the culture liquid containing the chemical substance is discharged, and then a fresh culture liquid is added. In this condition, the cells are further cultured in the 37° C. carbon dioxide incubator. The dish is picked out just after the addition of the chemical substance, at the end of the above treatment of the chemical substance, and on the first day, second day, third day, fifth day, seventh day and ninth day after the treatment in order to count the cells by use of a hemocytometer or an automatic cell measuring device by way of example. A cell growth curve is produced in a graph in which the abscissa and ordinate respectively indicate the number of days of culturing and the number of cells for a single laboratory disk. Numerical values representative of a period of time necessary for the number of cells to be doubled (cell doubling time) and a cell saturation density are read on the graph. The influence of the chemical substance is quantized on the basis of such numerical values in order to estimate the cytotoxicity of the substance.

A second cytotoxicity testing method uses a monolayer culture cell densitometer. After cells grown on a laboratory dish have been dyed by Crystal Violet, the degree of absorption of light having a wavelength of 555 nm by the dish is measured by the densitometer so as to determine the degree of growth of the cells. Specifically, cells are dispersed on a dish and cultured for 3 days in a carbon dioxide incubator. After a chemical substance to be tested has been added to a culture fluid in the dish, it is treated for 2 days, and then the culture fluid is discharged. After the cells have been fixed by an aqueous solution of formaldehyde, the cells are dyed by a Crystal Violet solution. After the dish has been dried by air, the degree of growth of the cells is measured by the above densitometer. For a control light absorption degree of 100%, the content of the chemical substance showing a light absorption degree of 50% is determined. The second method is often used to set the content of a substance to be treated in a chromosomal aberration induction test meant for a chemical substance.

A third cytotoxicity testing method uses Neutral Red to be taken into cells. Cells are implanted in the holes of a 96 hole microtiter plate together with a culture fluid and cultured for 48 hours in a 37° C. carbon dioxide incubator. Then, a culture fluid in which a chemical substance to be tested is dissolved is added, and 48 hours of culturing is effected. Subsequently, a Neutral Red solution is added, and 3 hours of culturing is effected. After excess Neutral Red has been discharged, the cells are fixed by an aqueous solution of formaldehyde. Neutral Red taken into the cells are extracted by a 50% ethanol and 1% acetic acid solution. The degree of absorption of light having a wavelength of 540 nm by the extracted liquid is measured by a microreader. Because Neutral Red passes only through the walls of live cells and deposits on lysosome, only live cells can be specifically dyed. A graph is produced in which the abscissa and ordinate respectively indicate the content of the chemical substance tested and the ratio of the amount of dye taken into the cells treated by the substance to the amount of dye taken into the cells not treated. The degree of toxicity is quantized as a chemical substance content setting up a ratio of 50% of the amount of dye taken into the treated cells to the amount of dye taken into the non-treated cells ($LD_{50}$ values).

A fourth cytotoxicity testing method uses Crystal Violet and is, in principle, substantially the same as the second method using the monolayer culture cell densitometer. Specifically, cells are sown in the holes of a 96 hole microtiter plate together with a culture liquid, and then a culture liquid containing a chemical substance to be tested is added. The cells are treated by the chemical substance for 3 days in a 37° C. carbon dioxide incubator. Subsequently, a glutaraldehyde solution is added to the holes of the above plate in order to fix the cells. After the fixing solution has been discharged, a Crystal Violet solution is introduced into the holes in order to dye the cells. After the dye liquid has been discharged, the plate is washed and then dried by air. A 96 hole microplate reader is used to measure the absorption of light having a wavelength of 590 nm by the dyed cells. For a control light absorption degree of 100%, the content of the chemical substance showing an absorption degree of 50% ($IC_{50}$) is determined.

A fifth cytotoxicity tensing method is a DNA assay method using a fluorescent dye. Grown cells are dyed by 2-diamidino-phenylindole (DAPI) or Hoechst 33342 which is a fluorescent dye. The fluorescence intensity of the resulting dyed cells is measured by a fluorescence photometer. Cells are sown in the holes of a 96 hole microtiter plate together with a culture fluid and cultured for 2 days in a 37° C. carbon dioxide incubator. After the culture fluid has been replaced with a new culture fluid containing a chemical substance to be tested, the chemical substance is caused to act on the cells for 3 days. Subsequently, the culture fluid is discharged, and then the cells are fixed by a glutaraldehyde solution. Thereafter, the cells are dyed by DAPI or Hoechst 33342 solution. The fluorescence intensity of the resulting dyed cells is measured by the above photometer. Finally, a cell density is determined on the assumption that a control fluorescence intensity is 100%.

A sixth cytotoxicity testing method forms colonies. Usually, cultured cells form irregular colonies in which cells high in viability and growability and cells low in the same exist together. Even cells with low viability can exist in a colony when cultured together with cells with high viability, because a culture environment is prepared by the surrounding cells. The sixth method uses the colony forming ability of cells as an index and is extensively applied to the measurement of the lethal effect of radiation or that of chemical substances. Specifically, cells reached a logarithmic growth stage are implanted in a laboratory dish together with a culture fluid and cultured in a 37° C. carbon dioxide incubator. After the cells have fully adhered to the dish and again started to grow, a culture liquid in which a chemical substance to be tested and having a preselected content is dissolved is added. On the elapse of a preselected period of time, the entire fluid is discharged and replaced with a new culture fluid. After the cells have been further cultured for 12 days to 14 days, the culture fluid is discharged. After cleaning and drying, the cells are fixed by methanol. The fixed colonies are dyed by a Giemsa dyeing liquid and counted. A survival rate curve is produced in a graph in which the abscissa and ordinate respectively indicate the content of the chemical substance to be tested and the logarithm of the ratio (survival rate) of the number of colonies on the treated dish to the number of colonies on a non-treated dish. Toxicity is quantized on the basis of the content of the chemical substance which lowers the survival rate to 50% or 37% ($LD_{50}$ value and $D_0$ value).

A seventh cytotoxicity testing method selectively dyes only dead cells (whose walls have some injury) and counts the number of dyed cells and that of non-dyed cells (live cells or cells whose walls are free from fatal injury), thereby determining the ratio of survived cells. Specifically, after cultured cells have been exposed to a chemical substance to be tested for a preselected period of time, they are dyed by a Trypan Blue solution. The cells whose cytoplasm and nuclei are entirely dyed in blue and the other cells are distinguished and counted by a hemocytometer individually. A survival rate is determined by:

$$\text{survival rate }(\%) = \frac{\text{total number of non-dyed cells}}{\text{total number of blue cells} + \text{total number of non-dyed cells}} \times 100 \quad \text{Eq. (1)}$$

Trypan Blue may be replaced with Eosine, erythrosine, Methylene Blue, Congo Red, Nigrosine or similar dye also capable of selectively dyeing dead cells.

An eighth cytotoxicity testing method is a $^{51}Cr$ isolation method. Specifically, after cells have been implanted in a culture flask, a 10 $\mu$Cia aqueous solution of $Na_2^{51}CrO_4$ is added. The cells are held for 20 to 24 hours in a 37° C., 95% air and 5% carbon dioxide incubator. As a result, $^{51}Cr$ is taken into the cells, and the $^{51}Cr$ index of the cells is completed. A $^{51}Cr$ index cell solution is introduced into the holes of a 96 hole microplate storing a chemical substance to be tested beforehand. Then, the cells are held for 4 to 24 hours in a 37° C., 95% air and 5% carbon dioxide incubator. After an absorbing material has been placed on the microplate, it is inserted into the holes by an exclusive press in order to absorb only the top. After the absorbing material has been transferred to a vial, radioactivity is measured by a gamma counter. A $^{51}Cr$ isolation ratio of the cells is determined by:

$$^{51}Cr \text{ isolation ratio }(\%) = \frac{\text{test group absorbent (cpm)} - \text{negative control absorbent (cpm)}}{\text{positive control absorbent (cpm)} - \text{negative control absorbent (cpm)}} \times 100 \quad \text{Eq. (2)}$$

The above $g^{51}Cr$ isolation ratio is used as the index of toxicity of the chemical substance. In the Eq. (2), the negative control is one to which a culture fluid not containing the chemical substance to be tested is added in order to measure the natural isolation of $^{51}Cr$ from injury-free live cells. The positive control is one to in which a culture solution containing 0.8% of phenol or 0.5% to 1.0% of Triton X-100 or similar surfactant is added to the cell culture fluid.

A ninth cytotoxicity testing method is a $^{51}Cr$ take-in method. While the above 51Cr isolation method is effective with chemical substances of the kind inducing cytolytic-death in a short period of time, it is low in sensitivity to substances of the kind not fully destroying cell walls. The $^{51}Cr$ take-in method is an improved version of the $^{51}Cr$ isolation method as to decision on live/dead cells. Specifically, after a cell solution has been introduced in the holes of a 96 hole microplate, a chemical substance solution to be tested is added. The plate is held at 37° C. for 1 hour to 8 hours, and then the top of the solution is removed by a centrifugal force. A culture fluid containing 1 $\mu$Ci of $Na_2^{51}CrO_4$ is introduced into the holes of the plate and held at 37° C. for 30 minutes. After $^{51}Cr$ not taken into the cells has been fully discharged, 50 $\mu$l of acetic acid is added to each hole and fully stirred. All the contents of the holes are transferred to gamma counter tubes in order to measure their radioactivity. Cytotoxicity is calculated as follows:

$$\text{cytotoxicity}(\%) = \frac{\text{test group }^{51}Cr \text{ take-in (cpm)}}{\text{negative control }^{51}Cr \text{ take-in (cpm)}} \times 100 \quad \text{Eq. (3)}$$

A tenth cytotoxicity testing method determines whether cultured cells are alive or dead by flow cytometry. When a Trypan Blue solution is added to a cell solution, only deal cells take it thereinto. Trypan Blue absorbs red helium-neon laser light having a wavelength of 632.8 nm and issuing from a flow cytometer. Therefore, a sample consisting of a number of cells is instantaneously divided into three groups of spots, i.e., live cells, dead cells, and cell fractions. The three groups of spots are drawn on an oscilloscope and allow a ratio between live cells and dead cells to be easily determined. When Hoechst 33342 and propidium iodide are used to dye DNA of unfixed cells, live cells and injured cells fluoresce in blue and red, respectively and can therefore be easily distinguished by a flow cytometer.

An eleventh cytotoxicity testing method is an agar diffusion method using agar culturing. With this method, it is possible to test the toxicity of a chemical substance without regard to its form, i.e., solid, powder, film, paste, liquid or the like. Cells are introduced into a laboratory dish together with a culture fluid and cultured for 24 hours in a 37° C. carbon dioxide incubator. After cleaning using a buffer liquid, the cell layer is covered with a culture solution to which Iw/V % of agar has been added, and then left for 20 minutes to 30 minutes to turn out a gel. After dyeing using Neutral Red, the excess dyeing liquid is removed. A chemical substance to be tested is put on the agar gel, and then the dish is turned upside down and cultured for 24 hours in the carbon dioxide incubator. The distances between the end of the chemical substance and decolored cells are measured by slide calipers or a phase contrast microscope in order to determine zone indices. The distances between the end of the chemical substance and non-destroyed cells are measured by the phase contrast microscope and used as lysis indices. The degrees of injury of the cells are estimated on the basis of the two index values (0 through 5).

Some improved versions of the agar diffusion method are available, as follows. An FDA (fluoresceindiacetate) dyeing method uses FD dyeing in places of Neutral Red dyeing. A collagen gel culture method uses collagen derived from animal tissue in place of agar. A Crystal Violet/SDS extraction method uses Crystal Violet dyeing in place of Neutral Red dyeing in order to improve the quantization of the agar diffusion method. Specifically, after cells have been treated by a chemical substance to be tested, Crystal Violet is extracted from the cells by 1% SDS (sodium dodecyl sulfate). Then, cytotoxicity is quantized on the basis of the degree of absorption of light whose wavelength is 598 nm.

A twelfth cytotoxicity testing method is an LDH method. LDH which is a lactic acid dehydrogenase or lysosome is released from cells to a culture fluid due to the wall injury of the cells. The LDH method examines cytotoxicity by using LDH activity as an index and is common to the dye exclusion method and $^{51}$Cl isolation method as to wall injury. Specifically, cells are introduced in the holes of a 24 hole dish together with a culture fluid and cultured for 48 hours in a 37° C. carbon dioxide incubator. After cleaning, a culture fluid containing a chemical substance to be tested is introduced into the holes and cultured for 4 hours. Thereafter, the cells and culture liquid are collected from the holes and then put in a centrifugal separator in order to measure the LDH activity of the top. The total LDH activity is corrected by naturally released LDH activity. The toxicity of the chemical substance is determined by producing an LDH release ratio, as follows:

$$\text{LDH release ratio (\%)} = \frac{\text{test } LDH - \text{control } LDH}{\text{total } LDH - \text{control} LDH} \times 100 \qquad \text{Eq. (4)}$$

A thirteenth cytotoxicity testing method uses a millipore filter and is a simple method for testing the cytotoxicity of a chemical substance implemented as a solid or a paste. A millipore filter is put in a laboratory dish, and then cells and a culture fluid are evenly dispersed on the filter and cultured for 24 hours in a 37° C. carbon dioxide incubator. After the culture fluid has been discharged from the dish, the filter is cleaned. Subsequently, the filter is turned upside down and for 24 hours in a 37° C. carbon dioxide incubator. After the culture fluid has been discharged from the dish, the filter is cleaned. Subsequently, the filter is turned upside down and put on flat agar prepared on a dish with its cell surface facing downward. A chemical substance to be tested is put on the filter and cultured for 2 hours in the carbon dioxide incubator. After the removal of the chemical substance, the filter is picked up from the agar. Succinic acid dehydrogenase reaction substrate solution is introduced into a dish, and then the filter is immersed in the solution with its cell layer facing upward and held at 37° C. for 3 hours. Thereafter, the filter is picked up from the dish, immersed in a formaldehyde solution, washed, and then dried. The cytotoxicity of the chemical substance is determined on the basis of a distance between the end of the substance and a non-dyed cell region.

A fourteenth cytotoxicity testing method uses MTT ([3-(4, 5-dimethylthiazol-2-yl )-2, 5-diphenyl tetrozorlium bromide]). MTT turns out formazan due to an enzyme present in intracellular mitochondria. After formazan has been dissolved in hydrochloric acid-isopropanol, calorimetric quantization is effected. The amount of formazan is dependent on the number of live cells and therefore representative of the same. Cells, a culture fluid and a chemical substance solution to be tested are introduced into the holes of a 96 hole microplate and cultured for 24 hours in acid-isopropanol solution, black crystals of formazan are dissolved by stirring. The degrees of absorption of 570 nm light and 630 nm light are determined by a microplate reader in order to quantize the toxicity of the chemical substance.

A fifteenth cytotoxicity testing method uses the obstruction effect against the migration of a radioactive precursor into cells, i.e., uses the inhibition of the synthesis of nucleic acids, proteins and so forth and sugar metabolism as an index. Migration of $^3$H-thymidine into DNA fractions or migration of $^3$H-uridine into RNA fractions is often used. As for the inhibition of protein synthesis, use is made of migration of $^3$H- or $^{14}$C-leucine or $^{35}$S-methionine. As for the inhibition of intercellular substrate formation, use is made of migration of $^{35}SO_4$ into glucose aminoglycan fractions or migration of $^3$H-proline into collagen fractions. Further, as for the inhibition of sugar metabolism, use is made of migration of $^{14}$C-glucose.

How $^3$H-thymidine is taken into cells will be described by way of example. A cell solution is introduced into the holes of a 96 hole microplate and cultured for 2 hours in a 37° C. carbon dioxide incubator. A chemical substance to be tested is added to each hole, and 4 hours of culturing is executed. After a culture solution containing 100 KBq/ml to 120 KBq/ml of $^3$H-thymidine has been added to each hole, 2 hours of culturing is effected in the incubator. After each hole has been evacuated and cleaned, the cells are peeled off from the plate by trypsin treatment and collected on a glass fiber filter. The filter is treated by ice-cooled 5% TCA in order to cause DNA to precipitate on the filter. The filter is cleaned, dried, and then put in a vial. After the addition of a scintillation cocktail, radioactivity is measured by a liquid scintillation meter. A ratio of the radioactivity of the cells treated by the chemical substance to a control is determined in order to quantize the toxicity of the chemical substance.

A sixteenth cytotoxicity testing method limits the amount of proteins and is a traditional method for the cytotoxicity test of anticancer medicine. A cell solution is filled in two test tubes, and then a chemical substance to be tested is introduced into the tubes. One of the tubes is put in a 37° C. carbon dioxide incubator for 72 hours for culturing. The other tube is put in a centrifugal separator in order to remove the culture fluid and then cleaned, and the resulting precipitated cells are held at 4° C. The tube subjected to 72 hours of culturing has also its cell layer cleaned. The amounts of proteins in the two tubes are quantized by colorimetric quantization on the basis of the degree of absorption (OD) of 650 nm light. A cell growth limitation ratio (%ICG) is produced by:

$$\% \ ICG = \frac{(62 \text{h test substance } OD) - (0 \text{ h test substance } OD)}{(72 \text{ h control } OD) - (0 \text{ h control } OD)} \qquad \text{Eq. (5)}$$

Ratios below 15%ICG are representative of "nonpoisonous", ratios of 15%ICG to 20%ICG are representative of "weakly poisonous", and ratios above 29%ICG are representative of "poisonous".

Japanese Patent Laid-Open Publication No. 7-123999 teaches another testing method using a base having a plurality of surface portions different in the easiness of adhesion of adhering cells. Cells, a culture fluid and a chemical substance to be tested are put in a container containing the above base and cultured. On the elapse of a preselected period of time, the base is observed in order to determine the toxicity of the chemical substance on the basis of the arrangement of the cells adhered to the base.

However, with the conventional cytotoxicity testing methods, particularly one determining the survival rate of cultured cells, it is impossible to directly or accurately count the prohibitive number of cohered live cells or dead cells one by one.

In practice, after live cells or dead cells have been colored by a dye, the degree of absorption of light whose wavelength is particular to the dye is measured in order to estimate the density of live cells or dead cells. However, this cannot be done unless a relation between the degree of light absorption by dyed cells and the actual cell density is determined beforehand. Moreover, the degree of light absorption by dyed cells does not provide a true cell density.

Technologies relating to the present invention are also disclosed in, e.g., Japanese Patent Laid-Open Publication NO. 63-295963.

SUMMARY OF THE INVENTION

It is therefore an object of the present invention to provide a cytotoxicity testing method capable of determining a cell survival rate by directly and accurately counting the number of live cells and that of dead cells one by one, and thereby quantizing the toxicity of a tested chemical substance with high accuracy.

A cytotoxicity testing method of the present invention has the steps of causing adhering cells to selectively adhere to the surface of a cell adhering film pattern provided on a base, and culturing the cells, culturing the cells in a culture fluid containing a chemical substance to be tested, dyeing the cells, and counting live cells and dead cells by observing the base to thereby determine a survival rate of the cells. As a result, the toxicity of the chemical substance is quantized.

BRIEF DESCRIPTION OF THE DRAWINGS

The above and other objects, features and advantages of the present invention will become apparent from the following detailed description taken with the accompanying drawings in which.

DESCRIPTION OF THE PREFERRED EMBODIMENTS

Figure 1:
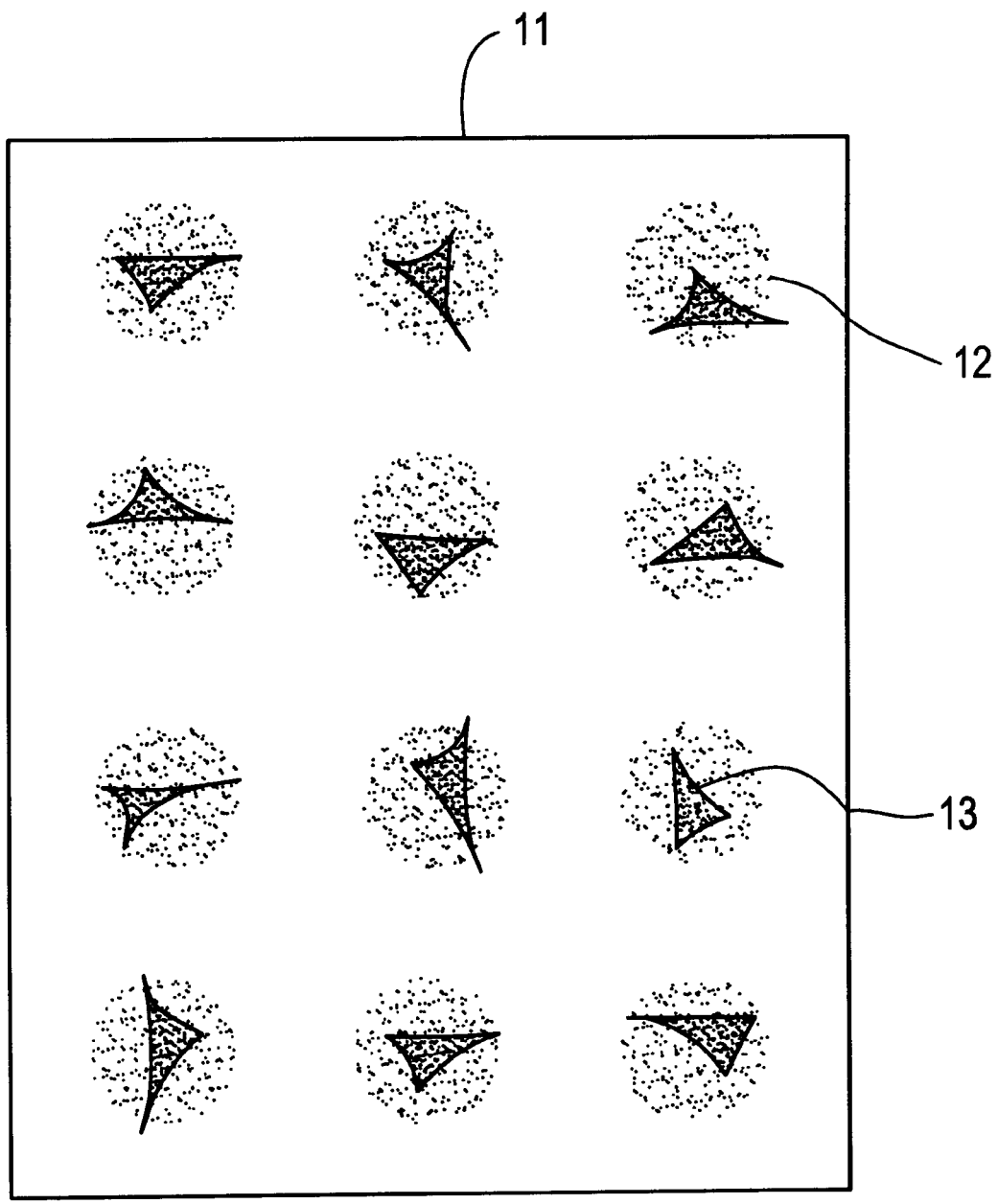
FIG. 1 is a plan view showing a device for practicing a cytotoxicity testing method embodying the present invention.

Referring to FIG. 1, a device for practicing a cytotoxicity testing method in accordance with the present invention is shown. As shown, a cell adhering film pattern 12 is prepared on the surface of a glass base 11. When adhering cells 13 are cultured on the glass base 11, they selectively adhere to the surface of the film pattern 12, but do not adhere to the base 11. The cells 13 adhered to the film pattern 12 are further cultured for a preselected period of time in a culture fluid containing a chemical substance to be tested. Subsequently, only the cells 13 present on the surface of the film pattern 12 are dyed, and then the number of live cells and that of dead cells are counted via a microscope. The toxicity of the chemical substance is quantized on the basis of the number of live cells and that of dead cells.

For the cell adhering film pattern 12, use may be made of collagen, fibronectin, laminin, vitronectin or similar cell adhering protein.

The adhering cells may be implemented by hepatic cells, vascular endothelial cells, fibroblasts, epidermal cells, epithelial cells, mammary gland cells, muscle cells, neurotubules, cartilage cells, and bone cells.

For a liquid for dyeing the cells, use may be made of any one of various kinds of liquids including Neutral Red, Crystal Violet, Trypan Blue, Eosine, eythrosine, Methylene Blue, Congo Red, Nigrosine, Alsian Blue, DAPI (2-diamidino-phenylindole), Hoechst 3342, and propidium iodide. The cell adhering film pattern and adhering cells may be used in any desired combination.

Preferred embodiments of the present invention will be described hereinafter.

1st Embodiment

Figure 2:
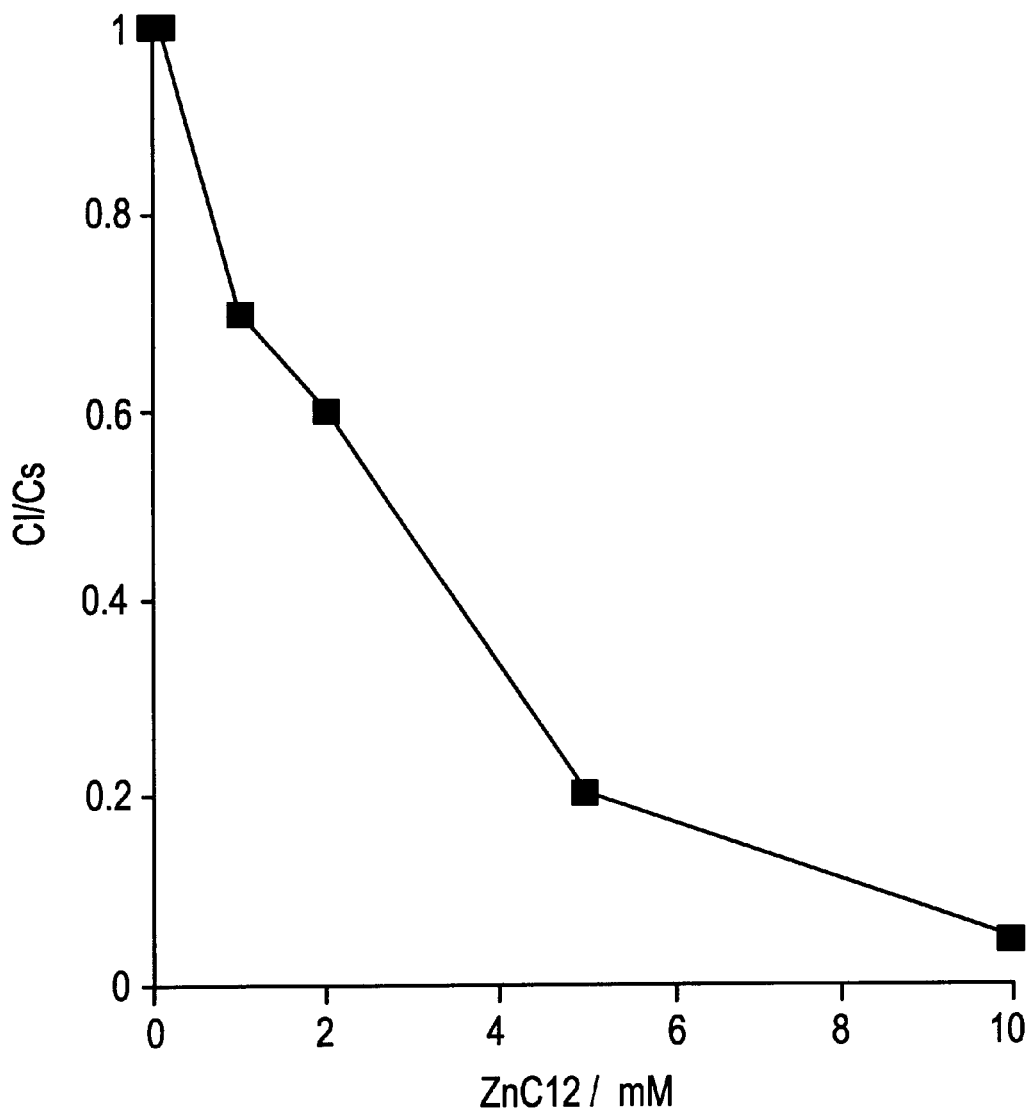
FIG. 2 is a graph showing a relation between the ratio (Cl/Cs) of the number of live cells to the total number of adhering cells and the content of a chemical substance to be tested (zinc chloride ($ZnCl_2$)).

Referring to FIGS. 1 and 2, a cytotoxicity testing method embodying the present invention will be described. In this embodiment, the cell adhering film pattern 12 and adhering cells 13 were respectively implemented by a collagen film pattern having films each having a diameter of 50 $\mu$m and HepG2 cells. The adhering cells were sown on the film pattern 12 together with an MEM (Minimum Essential Medium) culture fluid in a density of $1 \times 10^5$ cell/ml, and cultured for about 4 hours in a 37° C., 5% $CO_2$ and 100% $H_2O$ incubator. As a result, as shown in FIG. 1, one to two cells 13 specifically adhered to the surface of the film pattern 12 for a single film.

Subsequently, the culture fluid was sequentially replaced with MEM culture fluids respectively containing 0 mM, 0.1 mM, 1 mM, 2 mM, 5 mM and 10 mM of zinc chloride ($ZnCl_2$). In this condition, the cells were further cultured in the incubator for 20 hours to 24 hours. Then, a Neutral Red solution was added to the culture fluid such that the final content was 50 $\mu$g/ml, and then the cells were cultured for 3 hours. Neutral Red is taken only into live cells.

Finally, the ratio of the number of live cells (dyed by Neutral Red) to the total number of cells 13 on the film pattern 12 (Cl/Cs) was determined by use of a phase contrast microscope. A $ZnCl_2$ content-to-Cl/Cs curve shown in FIG. 2 was produced in order to quantize the cytotoxicity of $ZnCl_2$. As FIG. 2 indicates, 2 mM of $ZnCl_2$ reduces the survival rate Cl/Cs to about 60%.

2nd Embodiment

The cell adhering film pattern 12 and adhering cells 13 were respectively implemented by a collagen film pattern whose films each had a diameter of 50 $\mu$m and HepG2 cells, as in the first embodiment. The cells 13 were caused to selectively adhere to the surface of the film pattern 12 and cultured. The culture fluid was sequentially replaced with MEM culture fluids respectively containing 0 mM, , 0.1 mM, 1 mM, 2 mM, 5 mM and 10 mM of mercury chloride. In this condition, the cells were cultured in the incubator for 20 hours to 24 hours. Then, a Trypan Blue solution was added to the culture fluid such that the final content was 0.5%, and then the cells were cultured for 3 hours. Trypan Blue selectively dyes dead cells.

The ratio of the number of live cells (not dyed by Trypan Blue) to the total number of cells 13 on the film pattern 12 (Cl/Cs) was determined by use of a phase contrast microscope. A mercury chloride content-to-Cl/Cs curve shown in FIG. 2 was produced in order to quantize the cell toxicity of mercury chloride.

3rd Embodiment

The cell adhering film pattern 12 and adhering cells 13 were respectively implemented by a collagen film pattern whose films each had a diameter of 50 $\mu$m and the hepatic cells of a mature rat. The cells 13 were caused to selectively adhere to the surface of the film pattern 12 and cultured. The culture fluid was sequentially replaced with MEM culture fluids respectively containing 0 mM, 0.1 mM, 1 mM, 2 mM, 5 mM and 10 mM of copper chloride. In this condition, the cells were cultured in the incubator for 20 hours to 24 hours. Then, a Hoechst 33342 solution was added to the culture fluid such that the final content was 5 μg/ml, and then the cells were cultured for 2 hours. Hoechst 33342 specifically coupled with DNA present in the nuclei of live cells.

The ratio of the number of live cells (dyed by Hoechst 33342) to the total number of cells 13 on the film pattern 12 (Cl/Cs) was determined by use of a fluorescence microscope. A copper chloride content-to-Cl/Cs curve was produced in order to quantize the cytotoxicity of copper chloride.

4th Embodiment

The cell adhering film pattern 12 and adhering cells 13 were respectively implemented by an FITC index collagen film pattern whose films each had a diameter of 50 μm and the hepatic cells of a mature rat. The cells 13 were caused to selectively adhere to the surface of the film pattern 12 and cultured, as in the first embodiment. The culture fluid was sequentially replaced with MEM culture fluids respectively containing 0 mM, 0.1 mM, 1 mM, 2 mM, 5 mM and 10 mM of cadmium chloride. In this condition, the cells were cultured in the incubator for 20 hours to 24 hours in the incubator. Then, a Trypan Blue solution was added to the culture fluid such that the final content was 0.5%, and then the cells were cultured for 3 hours. Trypan Blue selectively dyes dead cells.

The ratio of the number of live cells (not dyed by Trypan Blue) to the total number of cells 13 on the film pattern 12 (Cl/Cs) was determined by use of a phase contrast microscope. A cadmium chloride content-to-Cl/Cs curve was produced in order to quantize the cytotoxicity of cadmium chloride.

It is difficult to observe a collagen film which is transparent, particularly a thin collagen film, with a transmission microscope. By using the FITC index collagen film pattern, it is possible to observe even such a film easily with a fluorescence microscope. This is an extremely effective implementation when the cell adhering film pattern 12 should be observed before the culturing of adhering cells.

5th Embodiment

The cell adhering film pattern 12 and adhering cells 13 were respectively implemented by an FITC index collagen film pattern whose films each had a diameter of 50 μm and the vascular endothelial cells of a human naval cord. The cells 13 were sown on the film pattern 12 evaluated through a fluorescence microscope together with a VE culture fluid in a density of 2×10⁴ cell/ml, and cultured for about 4 hours in a 37° C., 5% $CO_2$ and 100% $H_2O$ incubator. As a result, as shown in FIG. 1, one to two cells 13 specifically adhered to the surface of the film pattern 12 for a single film.

Subsequently, the culture fluid was sequentially replaced with VE culture fluids respectively containing 0 mM, 1 mM, 1 mM, 2 mM, 5 mM and 10 mM of carbon tetrachloride. In this condition, the cells were further cultured in the incubator for 20 hours to 24 hours. In this case, carbon tetrachloride was dissolved in DMSO implementing the final content of 0.5 volume % in the culture fluid and then added to the culture liquid. Then, a Neutral Red solution was added to the culture fluid such that the final content was 50 μ g/ml, and then the cells were cultured for 3 hours. Neutral Red is taken only into live cells .

Finally, the ratio of the number of live cells (dyed by Neutral Red) to the total number of cells 13 on the film pattern 12 (Cl/Cs) was determined by use of a phase contrast microscope. A carbon tetrachloride content-to-Cl/Cs curve was produced in order to quantize the cytotoxicity of carbon tetrachloride.

6th Embodiment

The cell adhering film pattern 12 and adhering cells 13 were respectively implemented by a collagen film pattern whose films each had a diameter of 50 μm and the vascular endothelial cells of a human naval cord. The cells 13 were caused to selectively adhere to the surface of the film pattern 12 and cultured, as in the fifth embodiment. The culture fluid was sequentially replaced with VE culture fluids respectively containing 0 mM, 0.1 mM, 1 mM, 2 mM, 5 mM and 10 mM of trichloroethane. In this condition, the cells were further cultured in the incubator for 20 hours to 24 hours in the incubator. Then, a DAPI solution implementing the final content of 5 μg/ml and 0.1 μM of propidium iodide solution were added to the culture fluid and cultured in the incubator for 3 hours. In this case, trichloroethane was dissolved in DMSO implementing the final content of 0.5 volume % in the culture fluid and then added to the culture fluid. DAPI is taken only into live cells while propidium iodide is taken into dead cells or injured cells . DAPI and propidium iodide fluoresce in blue and red, respectively Finally, the ratio of the number of live cells (observed through a blue filter) to the total number of cells 13 on the film pattern 12 (Cl/Cs) was determined by use of a fluorescence microscope. A trichloroethane content-to-Cl/Cs curve was produced in order to quantize the cytotoxicity of trichloroethane.

7th Embodiment

The cell adhering film pattern 12 and adhering cells 13 were respectively implemented by a collagen film pattern whose films each had a diameter of 50 μm and the vascular endothelial cells of a human naval cord. The cells 13 were caused to selectively adhere to the surface of the film pattern 12 and cultured, as in the fifth embodiment. The culture fluid was sequentially replaced with VE culture fluids respectively containing 0 mM, 0.1 mM, 1 mM, 2 mM, 5 mM and 10 mM of dichlorobenzene. In this condition, the cells were further cultured in the incubator for 20 hours to 24 hours. In this case, dichlorobenzene was dissolved in DMSO implementing the final content of 0.5 volume % in the culture fluid and then added to the culture liquid. Then, live cells and dead cells were respectively dyed by a DAPI solution and a propidium iodide solution, as in the sixth embodiment. The cells 13 were observed only on the surface of the film pattern 12. Thereafter, only the portions where the films 12 and cells 13 were present were swept by use of the automatic stage of a fluorescence microscope. The number of live cells (blue) and that of deal cells (red) were loaded in a computer by use of an automatic blue/green filter switching device and a microscope camera in order to automatically determine a ratio between them. A dechlorobenzene content-to-Cl/Cs curve was produced in order to quantize the cytotoxicity of dichlorobenzene.

As stated above, in the above embodiments, adhering cells are caused to selectively adhere to the surface of a cell adhering film pattern and cultured. After the treatment of a chemical substance to be tested, a ratio of the number of live cells to that of dead cells is determined. This procedure allows the cytotoxicity of the chemical substance to be easily quantized.

In summary, in accordance with the present invention, only one to several adhering cells are present only on a cell adhering film pattern for a single film. Live cells can therefore be accurately counted one by one in order to determine the survival rate of cells. This allows toxicity to be quantized with high accuracy. Further, when use is made of a microscope including an automatic stage and a camera for observation, the survival rate of live cells can be automatically determined, promoting rapid and easy quantization of cytotoxicity.

Various modifications will become possible for those skilled in the art after receiving the teachings of the present disclosure without departing from the scope thereof.

What is claimed is:

1. A cytotoxicity testing method comprising the steps of:
   (a) sowing adherent cells at a cell density on a glass base having a cell adhering film pattern comprised of a plurality of cell adhering films, wherein one to two of said cells selectively adheres to each of said films;
   (b) thereafter culturing said cells in a culture fluid containing a chemical substance to be tested;
   (c) staining said cultured cells with a liquid dye, said dye comprising a dye for staining live cells, a dye for staining injured cells, a dye for staining dead cells, or a dye for staining live and a dye for staining dead cells to obtain stained, chemically-treated cells; and
   (d) counting live cells and dead cells one by one by observing said base to thereby determine a survival rate of said cells, whereby toxicity of said chemical substance is quantitated on the basis of a microscopic visualization of each of said stained, chemically-treated cells adherent to each of said films.

2. The method as claimed in claim 1, wherein said cell adhering film pattern is formed of one of a protein selected from the group consisting of collagen, fibronectin, laminin and vitronectin.

3. The method as claimed in claim 2, wherein said cell adhering film pattern is formed of one of a fluorescence-labeled protein, further wherein said method comprises observing each of said films on said base by fluorescence microscopy before cell culturing.

4. The method as claimed in claim 1, wherein said adherent cells comprise one of hepatic cells, vascular endothelial cells, fibroblasts, epidermal cells, epithelial cells, mammary gland cells, muscle cells, neurotubules, cartilage cells, and bone cells.

5. The method as claimed in claim 1, wherein step (c) comprises staining said cells with a dye for staining dead cells.

6. The method as claimed in claim 1, wherein step (c) comprises staining said cells with a dye for staining live cells.

7. The method as claimed in claim 1, wherein step (c) comprises staining said cells with a dye for staining live cells and a dye for staining dead cells.

8. The method as claimed in claim 1, wherein step (d) comprises viewing said stained cells automatically by fluorescence microscopy and computerization.

* * * * *

UNITED STATES PATENT AND TRADEMARK OFFICE
CERTIFICATE OF CORRECTION

PATENT NO.: 6,132,979
DATED: October 17, 2000
INVENTOR(S): Toru MURAKAMI

It is certified that error(s) appears in the above-identified patent and that said Letters Patent is hereby corrected as shown below:

Column 3, line 65, delete "g"

Column 4, line 8, delete "51Cr" insert --$^{51}$Cr--.

Column 12, line 12, delete "1$^n$" insert --9--;

line 16, delete "1" insert --9--;

line 19, delete "1" insert --9--;

line 22, delete "1" insert --9--;

line 25, delete "1" insert --9--

Signed and Sealed this

First Day of May, 2001

Attest:

NICHOLAS P. GODICI

*Attesting Officer*       *Acting Director of the United States Patent and Trademark Office*